US010905209B2

(12) United States Patent
Vappie et al.

(10) Patent No.: US 10,905,209 B2
(45) Date of Patent: Feb. 2, 2021

(54) EXPANDABLE AND TRANSPORTABLE BAG

(71) Applicants: Jordan Vappie, Woodland Hills, CA (US); Heath Butler, Houston, TX (US)

(72) Inventors: Jordan Vappie, Woodland Hills, CA (US); Heath Butler, Houston, TX (US)

(*) Notice: Subject to any disclaimer, the term of this patent is extended or adjusted under 35 U.S.C. 154(b) by 0 days.

(21) Appl. No.: 16/373,591

(22) Filed: Apr. 2, 2019

(65) Prior Publication Data

US 2019/0313753 A1    Oct. 17, 2019

Related U.S. Application Data

(63) Continuation of application No. 15/805,126, filed on Nov. 6, 2017, now Pat. No. 10,244,837.

(60) Provisional application No. 62/491,250, filed on Apr. 28, 2017, provisional application No. 62/417,695, filed on Nov. 4, 2016.

(51) Int. Cl.
| | |
|---|---|
| *A45C 3/04* | (2006.01) |
| *A45C 7/00* | (2006.01) |
| *A45C 13/42* | (2006.01) |
| *A45F 5/00* | (2006.01) |
| *A45F 4/02* | (2006.01) |
| *A45C 13/10* | (2006.01) |
| *A01K 27/00* | (2006.01) |
| *A61F 5/37* | (2006.01) |
| *A45C 13/30* | (2006.01) |
| *A45C 9/00* | (2006.01) |
| *A63B 23/00* | (2006.01) |
| *A63B 21/02* | (2006.01) |
| *A63B 21/00* | (2006.01) |

(52) U.S. Cl.
CPC ............ *A45C 7/0077* (2013.01); *A01K 27/00* (2013.01); *A45C 3/04* (2013.01); *A45C 3/045* (2013.01); *A45C 9/00* (2013.01); *A45C 13/1046* (2013.01); *A45C 13/30* (2013.01); *A45C 13/42* (2013.01); *A45F 4/02* (2013.01); *A45F 5/00* (2013.01); *A61F 5/3738* (2013.01); *A45C 2013/306* (2013.01); *A45F 2005/006* (2013.01); *A45F 2200/0533* (2013.01); *A63B 21/02* (2013.01); *A63B 21/4023* (2015.10); *A63B 2023/006* (2013.01)

(58) Field of Classification Search
CPC ... A45C 7/0077; A45C 3/04; A45F 2005/006; A45F 3/02; A45F 2005/008; A44B 11/006; A41D 15/04
USPC ............. 224/219, 222, 600, 603, 660; 383/4
See application file for complete search history.

(56) References Cited

U.S. PATENT DOCUMENTS

| | | | | |
|---|---|---|---|---|
| 5,009,516 A | * | 4/1991 | Geeck .................. | A45C 3/04 206/37.1 |
| 5,092,681 A | * | 3/1992 | Ashley, III ............ | B65D 33/28 383/4 |
| 5,135,222 A | * | 8/1992 | Spector ................. | A63B 41/02 150/106 |

(Continued)

*Primary Examiner* — Adam J Waggenspack
(74) *Attorney, Agent, or Firm* — Gary P. Katz; Katz Law Group, LLC

(57) ABSTRACT

An expendable and transportable bag is disclosed. In one embodiment, a stretchable reusable bag hidden inside a lanyard keychain is now readily available to carry goods in a moment's notice of under 5 seconds. An attachment device enables the Sneakey-Bag to consistently be with the consumer, for example, with the consumer's keys or ID card and can be put away entirely in the lanyard in 3 to 5 seconds.

19 Claims, 6 Drawing Sheets

(56) References Cited

U.S. PATENT DOCUMENTS

| | | | | |
|---|---|---|---|---|
| 5,303,427 A * | 4/1994 | Fishbaine | ............. | A42B 1/006 2/171 |
| 6,186,662 B1 * | 2/2001 | Jackson | ................... | A45C 3/00 383/117 |
| 6,783,016 B2 * | 8/2004 | Wang | .................... | A42B 1/006 220/9.2 |
| 9,119,448 B1 * | 9/2015 | Hirshberg | ............ | A45C 7/0077 |
| 2007/0068944 A1 * | 3/2007 | McKinney | ............... | A45C 1/08 220/256.1 |
| 2012/0091174 A1 * | 4/2012 | Breeze | ................... | A01K 77/00 224/222 |
| 2015/0060504 A1 * | 3/2015 | James | ..................... | A45C 3/00 224/235 |

\* cited by examiner

EXPANDABLE AND TRANSPORTABLE BAG

CROSS REFERENCE TO RELATED APPLICATIONS

The present application is a United States Nonprovisional Patent Application that claims priority to co-pending U.S. patent application Ser. No. 15/805,126, entitled "An Expandable and Transportable Bag," filed on Nov. 6, 2017 which issued as U.S. Pat. No. 10,244,837 on Apr. 2, 2019 and claims priority to U.S. Provisional Patent Application Ser. No. 62/417,695, entitled "A stretchable reusable bag hidden inside a lanyard keychain to carry goods at a moment's notice," filed on Nov. 4, 2016 and U.S. Provisional Patent Application Ser. No. 62/491,250, entitled "An Expandable and Transportable Bag" filed on Apr. 28, 2017. U.S. patent application Ser. No. 15/805,126 along with U.S. Provisional Application Ser. Nos. 62/417,695 and 62/491,250 are hereby incorporated in their entirety by reference.

FIELD OF INVENTION

This invention generally relates to an expendable and transportable bag. More specifically, this invention relates to a stretchable reusable bag that can be placed inside a lanyard or keychain and used quickly or in a few seconds.

BACKGROUND OF THE INVENTION

Very often, consumers forget to retrieve their reusable bags from home, office or their car when shopping. Depending on the store, each plastic bag can cost up to 5 to 10 cents or the store may require the consumer to purchase a new reusable bag.

To avoid buying additional bags and to save money, consumers need to constantly plan and remember to bring the bags when shopping. This requirement can be a source of frustration to customers, even when it's a few items, a quick unexpected purchase and any other times when you need to carry goods.

Currently, reusable folding bags have complicated folds for the user to preform to put their bag away for the next time its needed. Some of these folds take over a minute or more to do. This time-consuming process can aggravate and frustrate the user to quickly fold or mush the bag back in its resting pouch. Most reusable bags require conscious thought before shopping, or gathering goods, to be brought. Often, a consumer must return to the trunk of their car, if they put it there from the previous time used, or pay the retailer for the bag needed to carry their goods.

Due to the popularity of lanyards, most people already have a lanyard when doing their daily activities. Prior art lanyards, only provide one function and cannot be used to store the bag.

Accordingly, there is a need for a device that can be easily stored and transported yet provides the strength to carry multiple items or heavy items. In addition, there is a need for a device to allow the expendable, easily transported bags to be attached to devices such as, keys, identification (ID) cards or other device consumers typical use to avoid forgetting the bags. This invention described below satisfies this need.

SUMMARY

In one embodiment, an apparatus is disclosed. The apparatus comprises, a mesh that can be removably inserted into a lanyard with at least two openings and a cavity inside the lanyard. In a more detailed embodiment, the apparatus comprises, a lanyard with at least two openings and at least one cavity inside the lanyard, mesh that is attached to the at least one cavity inside the lanyard, a first opening of the least two openings wherein the first opening slides over the mesh; and the mesh is removable from inside the lanyard.

In a second embodiment, a method is disclosed. The method comprises holding a lanyard, pulling both sides of a lanyard off the bar to remove the mesh bag, and fully pulling the bag off the lanyard by placing buckle and bottom strap inside lanyard. In an alternative method embodiment, the method comprises, holding a lanyard comprising two sides, wherein a first side comprises at least one elastic opening and a second side comprises a second elastic opening and at least one cavity between the two sides, pulling both sides of the lanyard away from each other to expose the mesh and pulling the mesh away from the lanyard to create a bag.

In a third embodiment, a method of manufacturing is disclosed. The method of manufacturing comprises: obtaining a mesh bag, adding a folder to both edges of the mesh bag, hemming multiple casing edges, running rope through casing, connecting all ends. In an alternative manufacturing method, the method comprises obtaining a mesh bag comprising at least two edges, adding a folder to the at least two edges of the mesh bag, hemming multiple casing edges to form a casing with a cavity, running rope through the cavity of the casing, and connecting both ends.

BRIEF DESCRIPTION OF THE DRAWINGS

The foregoing and other advantages of the present technique may become apparent upon reading the following detailed description and upon reference to the drawings in which.

DETAILED DESCRIPTION OF THE EMBODIMENTS

Figure 2:
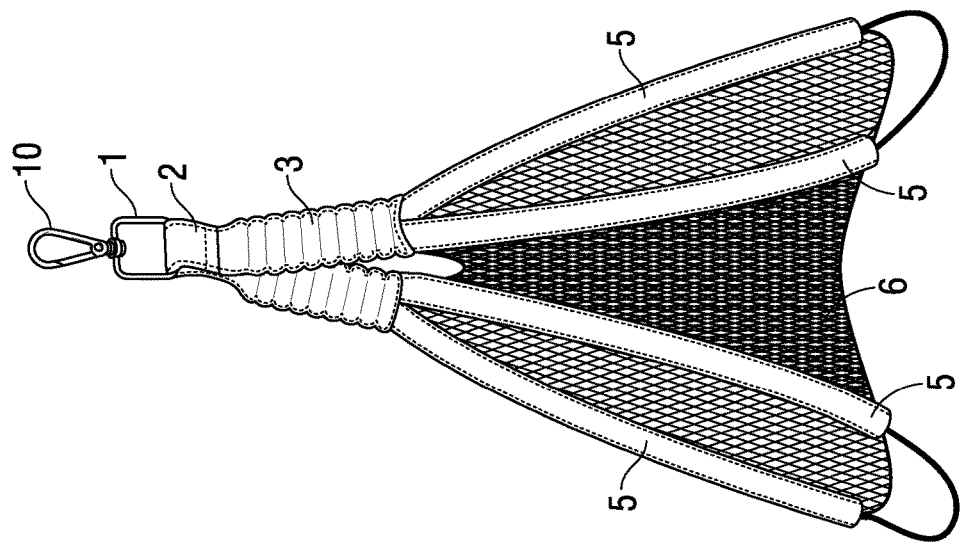
FIG. 2 illustrates the expandable bag being removed from the lanyard of FIG. 1.

Below is a description of various embodiments of the invention. Before describing selected embodiments of the present disclosure in detail, it is to be understood that the present invention is not limited to any embodiment described herein. The disclosures and descriptions herein are illustrative and explanatory of one or more presently preferred embodiments and variations thereof. It will be appreciated by those skilled in the art that various changes in the design, organization, means of operation, structures and location, methodology, and use of mechanical equivalents may be made without departing from the spirit of the invention.

The drawings are intended to illustrate and plainly disclose presently preferred embodiments to one of skill in the art, but are not intended to be manufacturing level drawings or renditions of final products. These may include simplified conceptual views to facilitate understanding or explanation. In addition, the relative size and arrangement of the components may differ from that shown and still operate within the spirit of the invention.

Moreover, various directions such as "upper", "lower", "bottom", "top", "left", "right", "first", "second" and so forth are made only with respect to explanation in conjunction with the drawings. The inventive components may be oriented differently, for instance, during transportation, manufacturing and operations. Numerous varying and different embodiments and modifications may be made within the scope of the concept(s) embodiments herein taught, and described. Therefore, it is to be understood that the details herein are to be interpreted as illustrative and non-limiting. For example, many embodiments and examples are used to describe a reusable shopping bag. However, the invention can be used to handle and transport many goods and not just consumer goods.

In one embodiment, this invention quickly and efficiently provides the consumer with an expendable and transportable bag that can be can be placed inside a lanyard or keychain and used quickly or in a few seconds. As stated above, consumers often (sometimes 9 times out 10 people) forget to retrieve their reusable bags from home, office or their car when shopping. Even if the consumer makes an unexpected trip to purchase only a handful of items, each bag forgotten can cost between 5 to 10 cents or require the purchase of an additional reusable bag at the store.

By allowing the bag to be attached to an item typically on the consumer, this reusable bag can always be available to the consumer. For example, attaching the reusable bag on the consumer's ID card holder, home and/or car key chain enables this reusable bag to quickly and easily be transported and retrieved at the checkout line or any place the user needs to carry goods.

In one embodiment, this invention is stylish enough to be on the user and easy to be put into action when needed and can be hidden when not needed. In most embodiments, there is no need for hard to remember folds to put away the reusable bag.

This invention provides improved functionality over currently available reusable bags to make it easily retrievable. Convenience is the main reason why most prior art commercially available reusable bags fail to work as well as advertised. The reusable bag describe herein can be opened in under 5 seconds and preferably under 3 seconds. In addition, the bag can be completely placed inside the lanyard in under 5 seconds and preferably under 3 seconds. In various embodiments, the lanyard also serves as a handle, a device for attaching and/or tying the bag to other devices and for closing the bag, as well as storage container for the bag. Alternatively, a simple pull down on the "Sneakey-Sleeve" reveals a multi-functional mesh or net bag that wraps around goods and secures them in transit. The consumer pulling the lanyard or sleeve back, will cause the sleeve to begin to bunch up towards the key-ring revealing a thin mesh netting. This netting appears looking like a second lanyard until the user whips the netting up and down. This motion is analogous to a person whipping up and down a folded paper bag to get it open. This single motion allows the user to spread the netting all the way open and prepare it for usage easily in under 5 seconds and as fast as 3 seconds.

After the bag is out of the sleeve the user will be able to place goods in the center of the bag. In one embodiment, a printed "bulls eye" or logo is in the center of the netting. The user can quickly pull on the cord handles on each side to secure the goods. By pulling on these cords the bag begins to tighten around the contents the user placed inside. This enables secure transportation without substantial movement of the goods, as is typically found in most reusable bags.

The draw string or cord or handles attached to the mesh have been made long enough to enable the user to have a plurality of carrying options. The cord should be at least 6 inches long, preferably at least 12 inches long and most preferably at least 18 inches long. The cord should preferably be less than 36 inches and more preferably less than 24 inches long to avoid the cord becoming difficult to handle. The cord can function as a carrying device and can be positioned over one shoulder, over both shoulders like a backpack, the common one-handed carry and combinations thereof.

Preferably, the bag should be made of netting or mesh material. Suitable materials include but are not limited to nylon, leather, micro-suede, spandex, non-woven fabric, linen, polyester, cotton, and any combination thereof. In one embodiment, this reusable expanded bag can carry a plurality of objects at least two-times the area inside the lanyard the bag fits in. In a preferred embodiment, this reusable expanded bag can carry a plurality of objects at least three-times the area inside the lanyard the bag fits in. In a more preferred embodiment, this reusable expanded bag can carry a plurality of objects at least three-times the area inside the lanyard the bag fits in.

In the lanyard mode, the "Sneakey-Bag" is able to attach or hold the user's keys, identification card or anything that can fit on a key-ring or other suitable attachment device. After the user removes goods, the user can hold the bag at the top by the key ring with one hand and pull down one or both sleeves with the other hand. This will hide the bag and return it back to lanyard mode.

The unique design can also be used to carry other bags if the user needs to carry a plurality of bags. The user accesses the additional bags by running the bag in lanyard mode through the handles of the other bags, looping back into the lanyard and then pulling. In this embodiment, the user can transport a plurality of bags, which in certain embodiments can be 4 bags, or preferably more than 4 bags at one time with this action.

Apparatus

Figure 1:
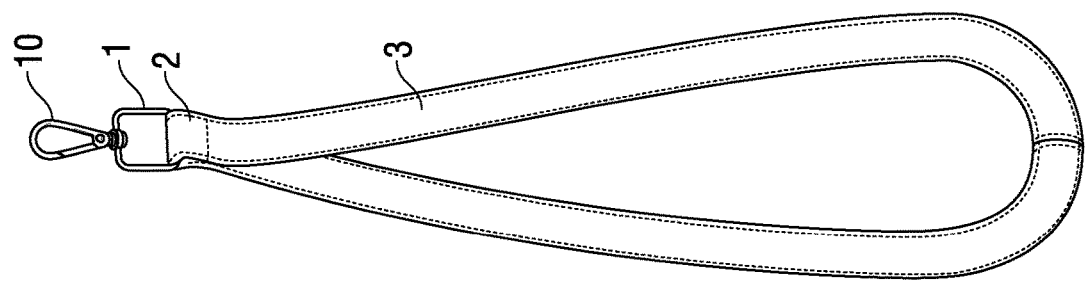
FIG. 1 illustrates a lanyard embodiment capable of holding and transporting the expandable bag.
Figure 4:
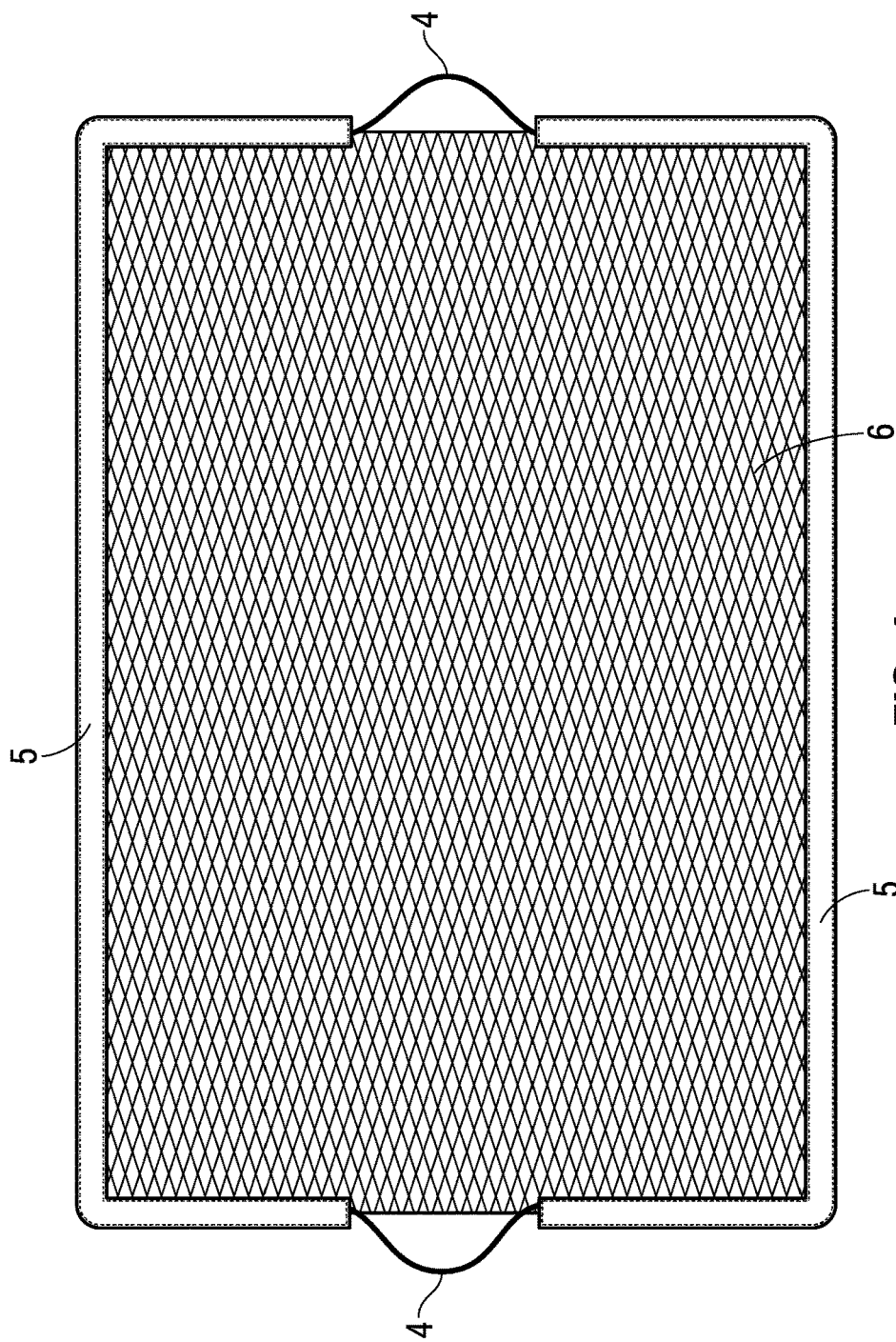
FIG. 4 illustrates individual components of an embodiment of the expandable bag.
Figure 3:
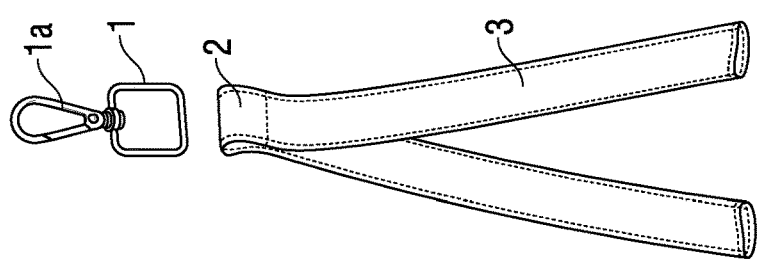
FIG. 3 illustrates the individual components of a lanyard embodiment.
Figure 5A:
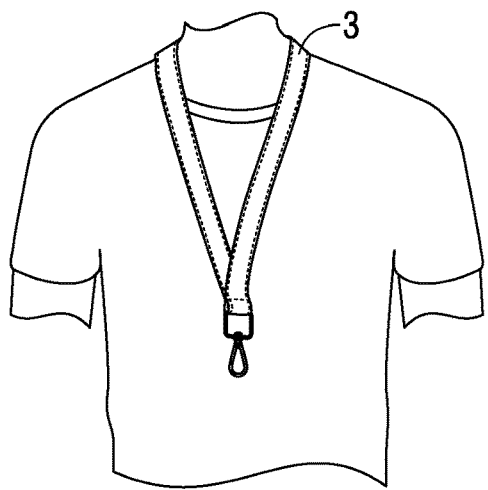
FIGS. 5A, 5B, 5C, 5D and 5E illustrate a method embodiment for opening the bag.
Figure 5B:
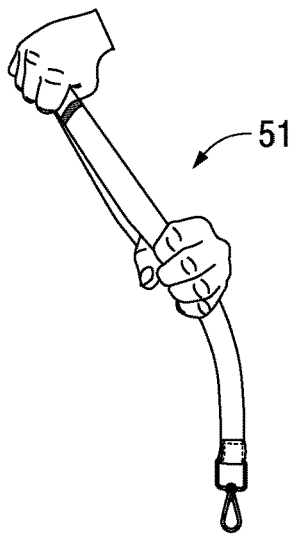
Figure 5C:
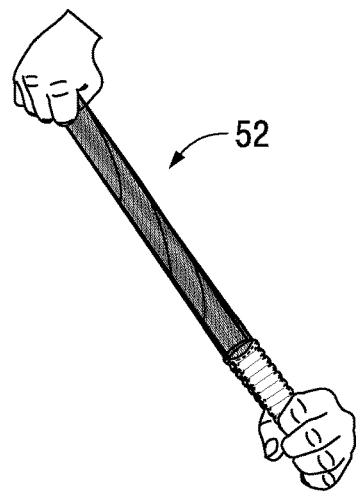
Figure 5D:
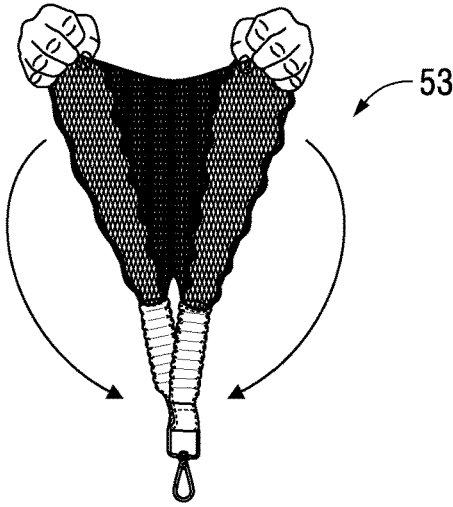
Figure 5E:
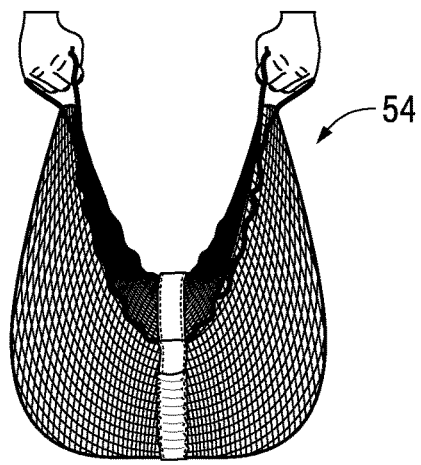

In one embodiment, as shown in FIG. 1, the apparatus comprises a lanyard. As shown in FIG. 1, the lanyard has a key ring 1, a loop or key ring fold 2, a cloth sleeve or lanyard 3 and an optional attachment device (such as, a clip) 1*a* attached to the key ring 1. In FIG. 1, the lanyard is shown with the two openings touching or closed which is obscured and thus, not shown in the drawings. FIG. 2 illustrates the reusable bag being partially deployed. The same or similar elements from FIG. 1 have been given the same reference numerals. FIG. 2 illustrates the mesh bag 6, the draw string housing 5 and the draw string 4. The mesh is removed from at least one opening and preferably from both openings on the lanyard. FIG. 3 illustrates the components of the lanyard before the reusable bag is fully manufactured or assembled. Likewise, FIG. 4 illustrates the components of the mesh bag before the reusable bag is fully manufactured and/or assembled. The same or similar elements from FIG. 1 and FIG. 2 have been given the same reference numerals in FIG. 3 and FIG. 4.

In one embodiment, the relationship between the components provide improved functionality, with FIG. 2 showing one possible relationship. As shown in FIG. 2 the key ring 1 is housed in the key ring fold 2 to secure key ring 1 from moving. The cloth sleeve 3 or lanyard can be used to hide the bag. The draw string is woven through drawing housing 5 that is attached to mesh netting 6 with the support string 7 that lays in the middle of the bag 9. Preferably, the majority or at least 50 percent of the mesh can be removed from inside the lanyard with the mesh still attached to the cavity inside the lanyard. More preferably, at least 80 percent of the mesh can be removed from inside the lanyard with the mesh still attached to the cavity inside the lanyard.

Method:

In one embodiment, the lanyard cloth sleeve is pulled back to unveil a hidden mesh bag that once deployed can stretch out to a larger cylindrical shaped bag that has a drawstring on each side that can be used to secure around goods inside the bag when pulled tight. In addition, the drawstrings can be utilized as shoulder straps. In one embodiment, the method comprises 4 steps, as shown in FIG. 5. First, the user grabs the lanyard from top to slide off sleeve 51. Second, the user slides both sides off releasing the mesh bag 52. Third, the user fully pulls the mesh bag out 53 (and optionally can flip the handle—placing the attachment device or loop or buckle and bottom strap inside the mesh). Fourth, the user inverts and holds by cord handle 54 and the user can then can place items inside the bag, as needed.

There are numerous benefits of putting the attachment device and bottom strap inside the mesh. Several benefits are discussed below. However, the discussion is not meant to include all the benefits as a person skilled in the art would recognize additional uses and benefits with the aid of the disclosure herein.

First, the bag can expand substantially by at least twenty percent and up to fifty percent larger due to the configuration of the bag. Second, the user can increase the size and volume of the items that can be placed in the bag. Third, the user may place more items in the expanded bag than they would typically place in an average or normal sized plastic grocery bag. Fourth, once the bag is fully packed, the user places the draw stings over the arms to carry the bag on his shoulders. Finally, once the bag is fully packed the drawstrings can be tied to further secure the items inside.

Figure 6A:
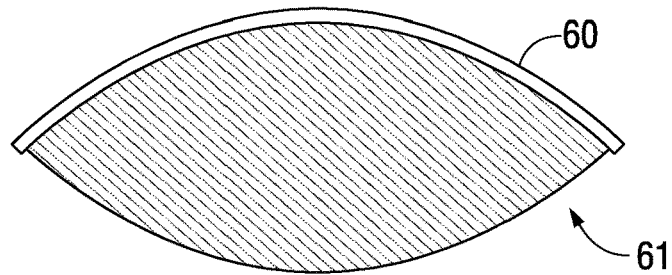
FIGS. 6A, 6B, 6C, 6D, 6E, 6F, 6G and 6H illustrate a method of manufacturing embodiment.
Figure 6B:
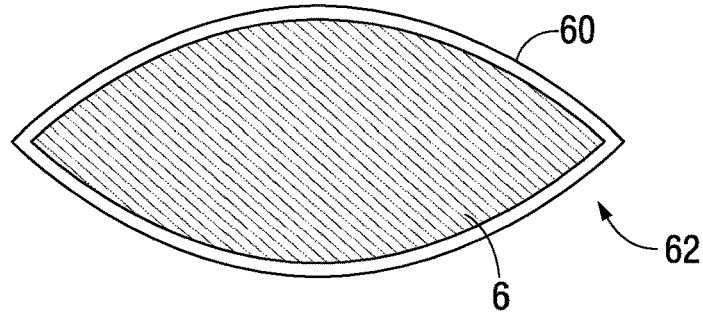
Figure 6C:
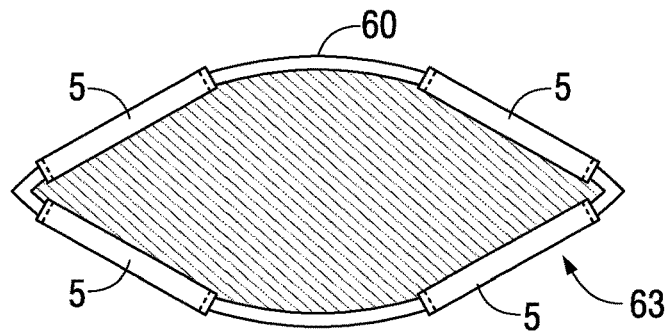
Figure 6D:
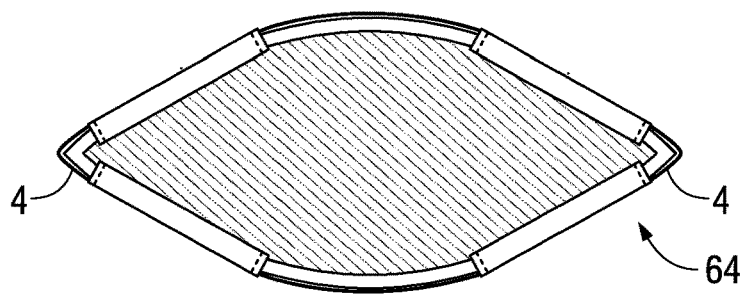
Figure 6E:
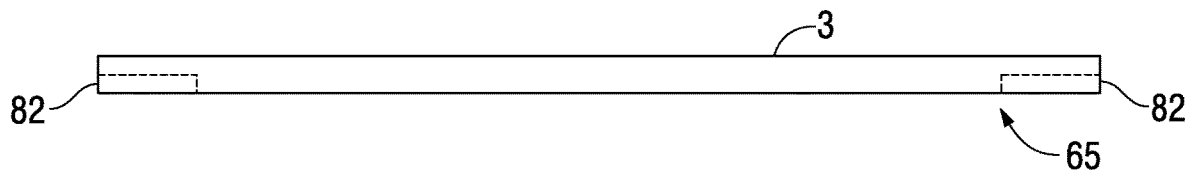
Figure 6F:
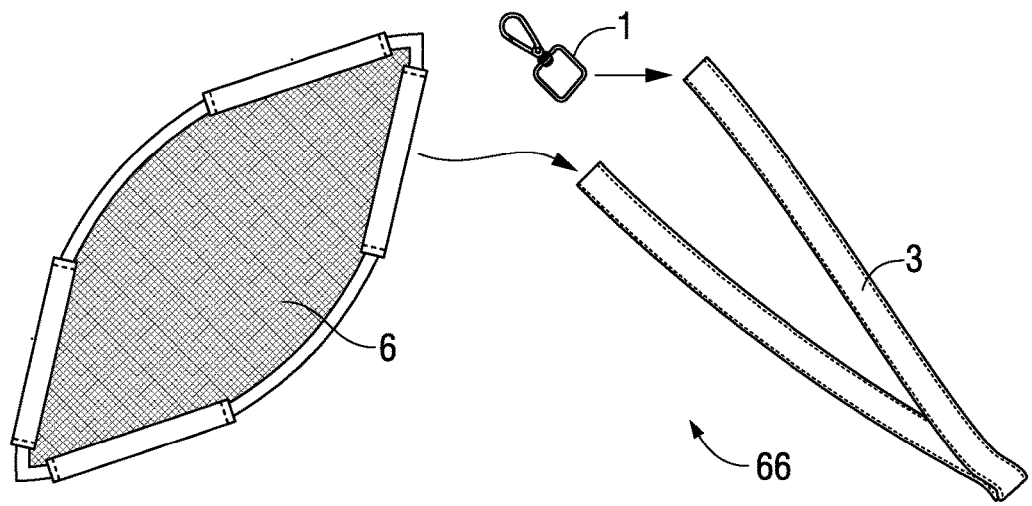
Figure 6G:
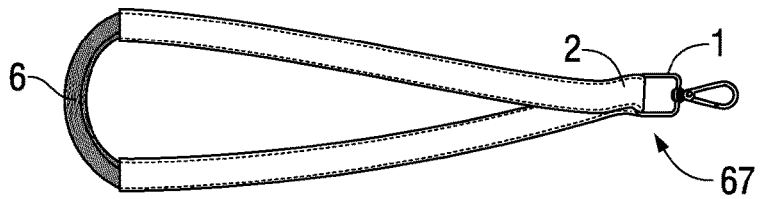
Figure 6H:
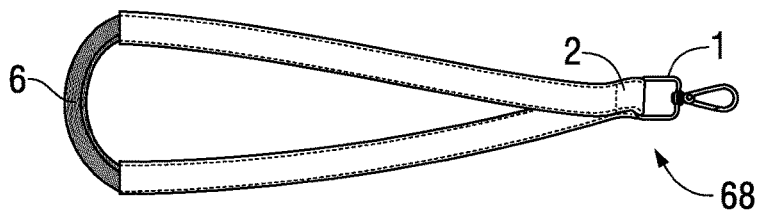

Method of Manufacture:

A method of manufacturing is disclosed. As shown in FIGS. 6A-6H, the method, in one embodiment, may contain 8 steps. First, a binding, folder or hem 60 is attached to a mesh net on one side—step 61, as shown in FIG. 6A. Second, the folder or hem 60 is applied to both sides of the mesh bag 6—step 62, as shown in FIG. 6B. A single needle or other attachment method can be used to attach the folder to both edges. Third, a plurality of casings or housings 5 are attached to the hems 60 at edges—step 63, as shown in FIG. 6C. In the example shown in FIG. 6C, casings at ¼ inch (or both edges) are set with a single needle. Fourth, a rope or cord or drawstring 4 is run into the casings or housings 5 and attached to the ends—step 64, as shown in FIG. 6D. In the example shown in FIG. 6D, the ends and rope are bar tacked together. Fifth, a plurality of slits 82 are created at the edges of the sleeves 3 and then closed and turned inside out—step 65, as shown in FIG. 6E. In the example, shown in FIG. 6E, slits 82 are hemmed at ¼ inch on both edges and closed with overlock and turned inside out. Sixth, the mesh bag 6 or netting is slid through inside the case or sleeve 3 and ring device 1 is slid over the case or sleeve 3—step 66, as shown in FIG. 6F. Seventh, a closed loop 2 is formed, and the ends are slide to the middle to expose the rope handles—step 67, as shown in FIG. 6G. Eight, the ring is secured to the folded case or loop 2, such as by sewing the loop 2 together—step 68, as shown in FIG. 6H.

Now referring to FIGS. 1-6F, in another method embodiment, cut the mesh netting to size, then roll the ends of the netting to make a boarder to attach drawstring housing 5 on both sides of netting 6. Then, weave rope, cord or drawstring 4 through drawstring housing 5 in a continuous loop leaving enough string at the top and bottom for attachment at the end of this process. Weave support string 7 through the middle of the netting 6, leaving enough on both side to tie off at the end of the process. Gather one side of the netting and crimp. Do essentially the same to the other side to form a hammock shape with the netting without gathering the drawstring 4.

The cloth sleeve 3 can be measured and cut from printed fabric. Sew a seam at the top and bottom of cloth sleeve 3. With cloth sleeve 3 turned inside out sew binding seam from top to bottom.

Fish or run mesh 6 through cloth sleeve 3. Once mesh 6 is sticking out the bottom and top, take key ring 1 and place it in the middle of cloth sleeve 3. Tie off drawstrings to each other and push mesh 6 back through cloth sleeve 3 until mesh 6 is in the middle of cloth sleeve 3. Now fold cloth sleeve 3 with key ring 1 in the middle to create key ring fold 2 then sew a locking seam.

In one embodiment, all elements are necessary to form and complete the Sneakey-Bag's unique carrying and storing functions. However, in various embodiment, various individual elements can be chosen to obtain favorable functionalities.

Using the Invention:

When the user needs a bag, or the user has left their reusable bag at home or in the car, the user simply reaches for their keys or ID badge with a lanyard or sleeve containing a bag that hold 5 to 10 times its weight and size. When finished, the user simply stores the bag away in 3 to 5 seconds without worrying about tricky folds or complicated bag housing.

Additional Uses:

The application predominately addresses the use of the device as a bag embodiment. However, there are many additional uses. Additional uses can include dog leash, arm sling, luggage strap, luggage identifier, stretching strap, camera strap, and any combination thereof.

Dog leash: Because of its high-quality design and sewing a user can hook the key chain hook to a dog's collar as a dog's leash.

Arm sling: the Sneakey Bag is long enough while being used as a lanyard that if the user has an arm in a cast she or he can comfortably place their arm between the two sleeves.

Luggage strap or luggage gathering strap: The Sneakey Bag's strength and flexibility allows it to do the tough job of gathering rolling luggage. The user can tread the Sneakey Bag through the handles or the strap holds of the rolling bags and bring it right back through Sneakey Bag and affix it to the main bag and then the luggage is ready to roll.

Luggage Identifier: The user can use the unique and vibrant colors Sneakey Bag options and tie tied the device to luggage to make the luggage readily identifiable. In addition, to both distinctive colors or a multiple combination of colors, the user can select distinctive styles such as, locks and chain designs.

Stretching strap: Sneakey Bag's length and shape fits comfortably around the sole of a user's feet while lying on their back and holding the other end of the Sneakey Bag in their hands to provide a stretch to the hamstrings, calves or other muscle groups. While standing, the user can take Sneakey Bag in one hand bring it behind the user's back going down. The other hand of the user can then be placed behind the user's back from the bottom reaching for the Sneakey Bag. Once the user has it in both hands behind the user's back the user can provide a pull at the bottom. This will stretch the triceps or other muscle group.

Camera strap: Sneakey Bag can be used to create a convenient and easy to use camera strap. The user can attach the key ring into the camera's hook and then the user is ready take a shot at any moment.

EXAMPLE

Figure 7:
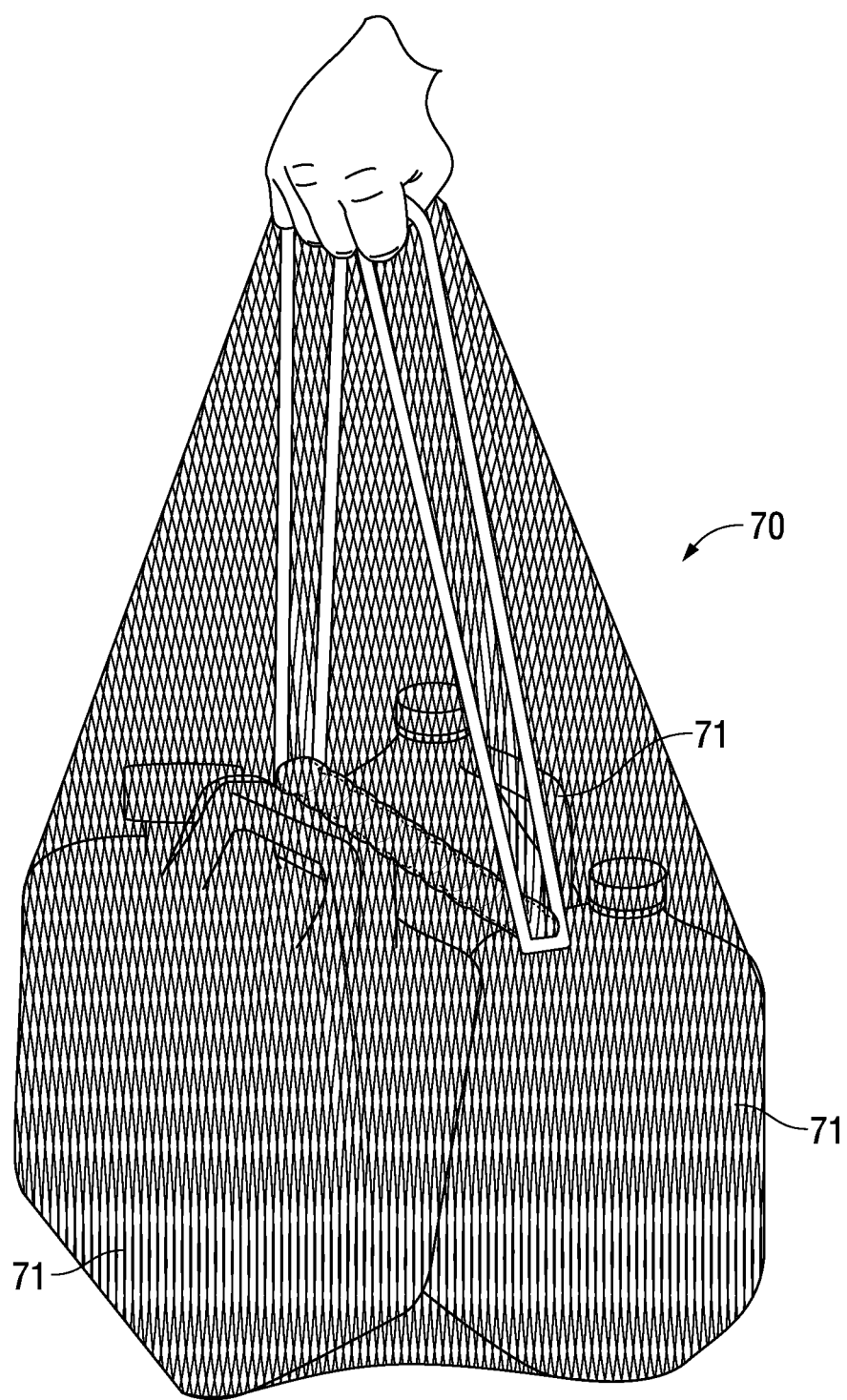
FIG. 7 illustrates an example embodiment being used to carry groceries.

A Sneakey-bag was created and tested. FIG. 7 is a top view of the Sneakey-bag 70 being used to carry groceries 71. The Sneakey-Bag is 22 inches in length around, 3.5 inches wide and was suitable for carrying significant amounts of the user's goods at a moment's notice. When pulling the sleeve back this sleeve will begin to bunch up about 2 to 3 inches on both sides towards the key-ring revealing a thin gauge of 22−6=16 mesh netting. Other suitable gauges can be used. This action is performed smoothly because of the 100% polyester mesh netting mixed with the 100% grosgrain tape of the outer covering used to reduce friction when moving the "sneakey sleeve" back and forth. When opened, the bag has a base of 22 inches wide and 22 inches deep.

The 5-mm cord handles that are embedded inside the seams of the netting on each side to secure the user's goods. The cord handles are 5 mm thick and 100% polyester and have been measured and designed for comfort to the hand and shoulders to prevent any irritation. They have been designed to be long enough so that the user can have carrying options. Furthermore, a double headed plastic hook allows the user to secure their goods and prevent spillage out of the top of the bag.

Test have shown the ability to carry over 25 lbs of goods and odd shaped items that might not fit in a traditional goods bag. The "Sneakey Bag's" netting has been designed to be small enough to hide under the 100% grosgrain tape with sublimation print and big enough to carry a full bag and a half of groceries or other daily goods users and consumers may need to carry.

When in lanyard mode, the "Sneakey-Bag" is able to hold the user's keys, ID card or anything that can fit on a key-ring. Putting the bag back in lanyard mode will take 3 to 5 seconds. The user, after taking out goods can hold the bag at the top by the key ring with one hand and pull down one or both sleeves with the other hand. This will hide the bag and return it back to lanyard mode. In lanyard mode, the "Sneakey Bag" is so easy to store in the pocket, purse, rear-view mirror or around the user's neck. All these places are traditional areas where users place their work ID cards and minus the rear-view mirror the user's keys.

We claim:

1. A method comprising:
   a. obtaining a mesh bag comprising at least two edges,
   b. adding a folder to one of the at least two edges of the mesh bag,
   c. hemming hemming multiple casing edges to the folder to form a casing with a cavity,
   d. running rope through the cavity of the casing, and
   e connecting both ends of the casing with cavity using the rope,
   f. placing at least two sleeves around the casing with a cavity, wherein the mesh bag fits inside the at least two sleeves
   g. holding the sleeves together to form a lanyard comprising two sides, wherein a first side comprises at least one elastic opening and a second side comprises a second elastic opening and at least one cavity between the two sides;
   h. pulling both sides of the lanyard away from the mesh to expose the mesh;
   i. inserting a finger into the first elastic opening of the first side; and
   j. pulling the mesh bag off the lanyard.

2. The method of claim 1, further comprising attaching the lanyard using an attachment device and wherein both the first elastic opening and the second elastic opening slides along the mesh inside the lanyard.

3. The method of claim 1, further comprising using the mesh as a bag by placing at least one item in the mesh and pulling a string attached to the mesh to close the mesh around the at least one items in the bag.

4. The method of claim 3, wherein the attachment device is connected between the first elastic opening and the second elastic opening.

5. The method of claim 4, wherein the attachment device comprises a key ring, a key ring fold, and a cloth sleeve attached to the lanyard.

6. The method of claim 1 wherein the mesh bag is pulled off the lanyard and the mesh back is completely exposed in under three seconds.

7. The method of claim 1 further comprising using the lanyard as a dog leash, arm sling, luggage strap, luggage identifier, stretching strap, camera strap, and any combination thereof.

8. A method of manufacturing comprising:
   a. obtaining a mesh bag comprising at least two edges,
   b. adding a folder to one of the at least two edges of the mesh bag,
   c. hemming multiple casing edges to the folder to form to form a casing with a cavity,
   d. running rope through the cavity of the casing, and
   e connecting both ends of the casing with cavity using the rope,
   f. placing at least two sleeves around the casing with a cavity, wherein the mesh bag fits inside the at least two sleeves to form a lanyard.

9. The method of claim 8, further comprising folding at least one sleeve and sewing a key ring fold to the at least sleeve with a fold, wherein the key ring fold holds the key ring attached to an attachment device.

10. The method of manufacturing of claim 8 wherein the material of the mesh bag comprises fabric selected from the group consisting of nylon, leather, micro-suede, spandex, non-woven fabric, linen, polyester, cotton, and any combinations thereof.

11. A device comprising:
   a. a lanyard with at least two openings and at least one cavity inside the lanyard that is manufactured according to the method of claim 8.

12. The device of claim 11, wherein at least 50 percent of the mesh can be removed from inside the lanyard with the mesh still attached to the cavity inside the lanyard.

13. The device of claim 11, wherein at least 80 percent of the mesh can be removed from inside the lanyard with the mesh still attached to the cavity inside the lanyard.

14. The device of claim 11, wherein the mesh is attached to a section within the first opening of the lanyard and a section of a second opening of the at least two openings of the lanyard.

15. The device of claim 14, wherein a border of the mesh comprises a material that forms an outside edge of a mesh bag and the border is attached to the mesh bag, attached to the section within the first opening of the lanyard and attached to the section within the second opening of the lanyard.

16. The device of claim 15, wherein an attachment device is connected to the lanyard between the first opening of the lanyard and the second opening of the lanyard.

17. The device of claim 11, wherein the mesh comprises a fabric selected from the group consisting of nylon, leather, micro-suede, spandex, non-woven fabric, linen, polyester, cotton, and any combinations thereof.

18. The device of claim 11, wherein the lanyard comprises a key ring, a key ring fold, a cloth sleeve.

19. The device of claim 11, wherein the mesh expands to hold a plurality of objects at least two-times larger than the area inside the lanyard.

* * * * *